(12) United States Patent
Piron et al.

(10) Patent No.: US 9,314,530 B2
(45) Date of Patent: Apr. 19, 2016

(54) COMPOSITION, IN AQUEOUS MEDIUM, THAT COMPRISES AT LEAST A HYALURONIC ACID AND AT LEAST AN HYDROSOLUBLE SALT OF SUCROSE OCTASULFATE

(71) Applicant: LABORATOIRES VIVACY, Archamps (FR)

(72) Inventors: Estelle Piron, Saint Etienne De Cuines (FR); Jeremie Bon Betemps, Albens (FR)

(73) Assignee: LABORATOIRES VIVACY, Archamps (FR)

(*) Notice: Subject to any disclaimer, the term of this patent is extended or adjusted under 35 U.S.C. 154(b) by 124 days.

(21) Appl. No.: 13/916,236

(22) Filed: Jun. 12, 2013

(65) Prior Publication Data

US 2014/0005140 A1 Jan. 2, 2014

Related U.S. Application Data

(60) Provisional application No. 61/659,140, filed on Jun. 13, 2012.

(30) Foreign Application Priority Data

Jun. 13, 2012 (FR) ...................................... 12 55543

(51) Int. Cl.
| | |
|---|---|
| A61K 47/36 | (2006.01) |
| A61K 8/60 | (2006.01) |
| A61K 8/73 | (2006.01) |
| A61Q 19/08 | (2006.01) |
| A61K 31/7016 | (2006.01) |
| A61K 31/728 | (2006.01) |
| A61K 45/06 | (2006.01) |
| A61K 31/167 | (2006.01) |

(52) U.S. Cl.
CPC . *A61K 47/36* (2013.01); *A61K 8/60* (2013.01); *A61K 8/735* (2013.01); *A61K 31/167* (2013.01); *A61K 31/7016* (2013.01); *A61K 31/728* (2013.01); *A61K 45/06* (2013.01); *A61Q 19/08* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 2,715,091 A | 8/1955 | Ricketts et al. | |
| 5,916,880 A | 6/1999 | Bar-Shalom et al. | |
| 8,052,990 B2 | 11/2011 | Hermitte et al. | |
| 2005/0187150 A1* | 8/2005 | Mohammadi et al. | 514/12 |
| 2006/0040894 A1* | 2/2006 | Hunter et al. | 514/54 |
| 2006/0194758 A1 | 8/2006 | Lebreton | |
| 2010/0184720 A1 | 7/2010 | Gavard Molliard et al. | |
| 2010/0303873 A1 | 12/2010 | Piron et al. | |
| 2012/0245120 A1 | 9/2012 | Fabre et al. | |

FOREIGN PATENT DOCUMENTS

| | | |
|---|---|---|
| EP | 0 230 023 A2 | 7/1987 |
| EP | 0 640 346 A1 | 3/1995 |
| EP | 2 070 518 A2 | 6/2009 |
| FR | 2 865 737 | 8/2005 |
| FR | 2 983 483 | 6/2013 |
| WO | WO 89/05645 | 6/1989 |
| WO | WO 89/05646 | 6/1989 |
| WO | WO 94/00476 | 1/1994 |
| WO | WO 98/22114 | 5/1998 |
| WO | WO 00/46253 | 8/2000 |
| WO | WO 03/000191 A2 | 1/2003 |
| WO | WO 03/041724 A1 | 5/2003 |
| WO | WO 03/068243 A1 | 8/2003 |
| WO | WO 2004/034980 A2 | 4/2004 |
| WO | WO 2004/092222 A2 | 10/2004 |
| WO | WO 2005/061611 A1 | 7/2005 |
| WO | WO 2006/017752 A2 | 2/2006 |
| WO | WO 2008/157775 A1 | 12/2008 |
| WO | WO 2009/024670 A2 | 2/2009 |
| WO | WO 2009/068215 A1 | 6/2009 |
| WO | WO 2009/071697 A1 | 6/2009 |
| WO | WO 2011/069921 A1 | 6/2011 |
| WO | WO 2011/086458 A1 | 7/2011 |
| WO | WO 2011/101594 A1 | 8/2011 |
| WO | WO 2013/079889 A1 | 6/2013 |

OTHER PUBLICATIONS

Moseley et al., "The chemical modification of glycosaminoglycan structure by oxygen-derived species in vitro." Biochimica et Biophysica Acta, 1995, pp. 245-252, vol. 1244.

Servaty et al., "Hydration of polymeric components of cartilage—an infrared spectroscopic study on hyaluronic acid and chondroitin sulfate." International Journal of Biological Macromolecules, 2001, pp. 121-127, vol. 28.

Toida et al., "Inhibition of Hyaluronidase by Fully O-Sulfonated Glycosaminoglycans." Archives of Biochemistry and Biophysics, Oct. 15, pp. 176-182, vol. 370.

Zimmermann et al., "Inhibition of Hyaluronidase by Dextransulfate and Its Possible Application in Anticancer Treatment." J. Cancer Research Clinical Oncology, 1983, pp. 189-190, vol. 105.

Walton, K.W., "Investigation of the Toxicity of a Series of Dextran Sulphates of Varying Molecular Weight." Brit. J. Pharmacol, 1954, pp. 1-14, vol. 9.

(Continued)

*Primary Examiner* — Eric Olson
*Assistant Examiner* — Dale R Miller
(74) *Attorney, Agent, or Firm* — Oliff PLC

(57) ABSTRACT

A composition including at least one crosslinked or non-crosslinked hyaluronic acid, or one of its salts, and at least one water-soluble salt of sucrose octasulphate, to processes for the manufacture of said composition and to the use of said composition for the formulation of a viscosupplementation composition or for the formulation of a composition as a dermal filler or for the formulation of a cosmetic composition.

26 Claims, 2 Drawing Sheets

(56) References Cited

OTHER PUBLICATIONS

Figure 1:
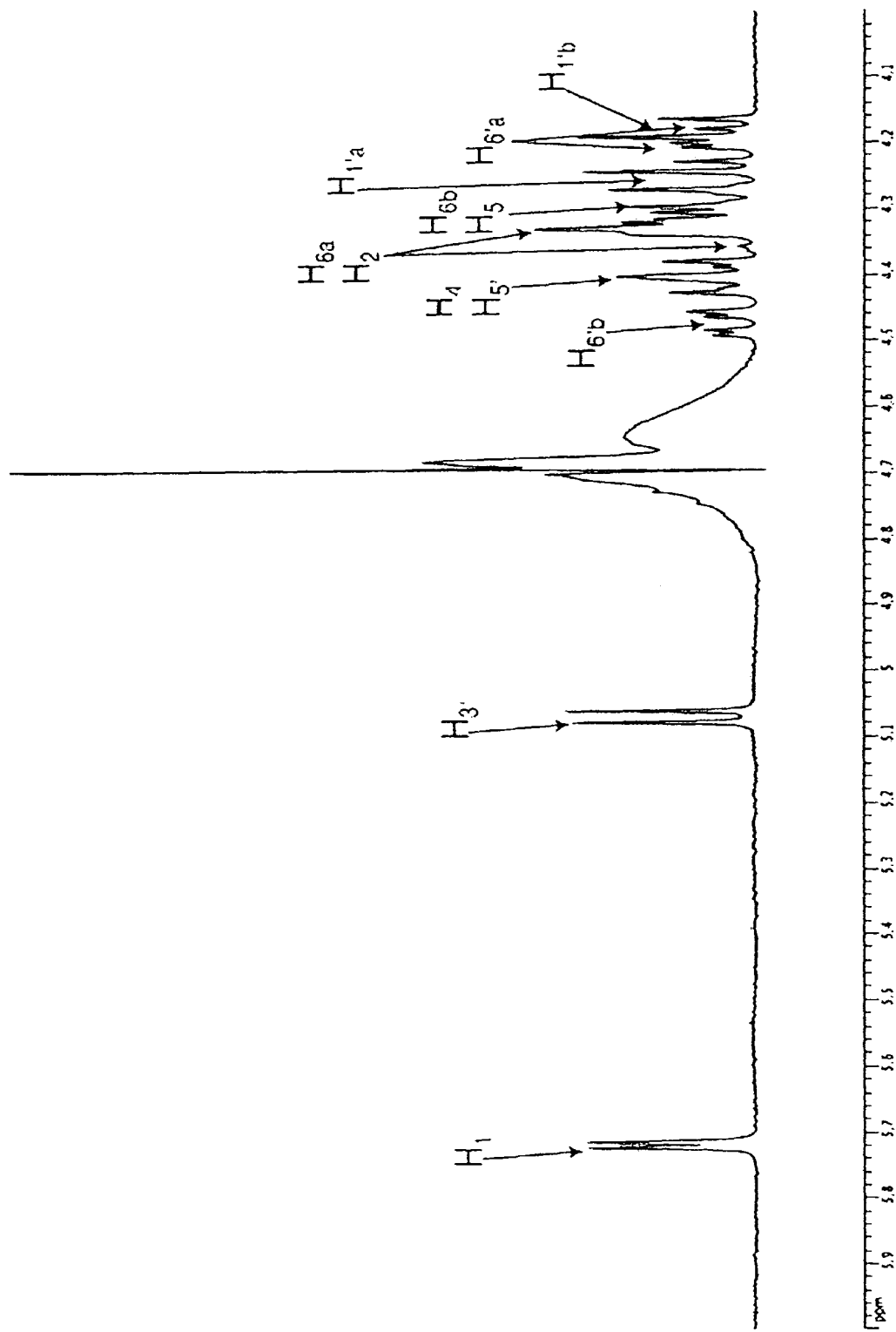

Salmen et al., "Sulphated Oligosaccharides as Inhibitors of Hyaluronidases from Bovine Testis, Bee Venom and *Streptococcus agalactiae*." Planta Medica, 2005, pp. 727-732, vol. 71.

Suzuki et al., "Preparation and inhibitory activity on hyaluronidase of fully O-sulfated hyaluro-oligosaccharides." Glycobiology, 2001, pp. 57-64, vol. 11.

Fenton et al., "The effects of glucosamine derivatives on equine articular cartilage degradation in explant culture." Osteoarthritis and Cartilage, 2000, pp. 444-451, vol. 8.

Sall et al., "Comparison of the sensitivity of 11 crosslinked hyaluronic acid gels to bovine testis hyaluronidase." Polymer Degradation and Stability, 2007, pp. 915-919, vol. 92.

Fannon et al., "Sucrose Octasulfate Regulates Fibroblast Growth Factor-2 Binding, Transport, and Activity: Potential for Regulation of Tumor Growth." J Cell Physiol, May 2008, pp. 434-441, vol. 215.

Yeh et al., "Structural Basis for Activation of Fibroblast Growth Factor Signaling by Sucrose Octasulfate." Molecular and Cellular Biology, Oct. 2002, pp. 7184-7192, vol. 22.

Iocono et al., "Hyaluronan Induces Scarless Repair in Mouse Limb Organ Culture." Journal of Pediatric Surgery, Apr. 1998, pp. 564, vol. 33.

\* cited by examiner

COMPOSITION, IN AQUEOUS MEDIUM, THAT COMPRISES AT LEAST A HYALURONIC ACID AND AT LEAST AN HYDROSOLUBLE SALT OF SUCROSE OCTASULFATE

Hyaluronic acid has been used for more than fifteen years in the aesthetics field, where it has proved to be harmless and effective. Currently, gels based on crosslinked hyaluronic acid originating from biofermentation are the most widely used products in the aesthetic filler gel market or as fillers. Indeed, in the aesthetics field, non-resorbable implants are used less and less and gels based on other polysaccharides have been abandoned, either because of side effects or because of their animal origin, resulting in the risk of viral contamination.

The use of hyaluronic acid resulting from biofermentation in fields such as dermal fillers, viscosupplementation, ophthalmic treatment or the treatment of urinary incontinence is all the more recognized and valued as, due to its natural presence in the human body, more particularly in the dermis, synovial fluid and cornea, risks due to side effects are minimized.

However, owing to the fact that hyaluronic acid is naturally present in the body, there exist endogenous enzymes capable of decomposing it, such as, for example, the hyaluronidases. This decomposition is illustrated in Iocono et al., J. Ped. Surg., Vol. 33, No. 4, 1988, 564-567, which relates to the healing of wounds. Hyaluronidases are enzymes which decompose hyaluronic acid by catalysing its hydrolysis to give oligosaccharides of hyaluronic acid. This decomposition has the effect of decreasing the viscosity of hyaluronic acid. This decrease in viscosity irremediably results in a decrease over time in the effects desired in the fields of dermal fillers or viscosupplementation, resulting in a shortening in the time between injections, in order to restore the effect thereof, liable to cause annoyance or pain to the patient.

A first solution for solving this problem might be to replace hyaluronic acid with other polysaccharides which are less sensitive to the hyaluronidases and which are naturally present in the human body.

Among the constituent polysaccharides of the ExtraCellular Matrix (ECM), Chondroitin sulphate, Dermatan sulphate and Keratan sulphate might be advantageous.

This is because they are partly responsible, along with hyaluronic acid, for hydration and suppleness of the skin and their natural presence in the dermis makes it possible to foresee excellent tolerance and effectiveness for a product as a dermal filler, for rehydration or for viscosupplementation.

Unfortunately, chondroitin sulphate is of animal origin and none of the attempts to synthesize chondroitin sulphate by the biofermentation route have, to date, made it possible to produce it in amounts compatible with industrial exploitation. The same applies to dermatan sulphate and keratan sulphate, which are only available industrially as products of animal origin.

Another solution targeted at reducing the decomposition of hyaluronic acid by hyaluronidases is to provide compositions comprising, in combination with hyaluronic acid, a compound having hyaluronidases-inhibitor properties.

Sulphate groups are known in the literature for their antioxidant and anti-radical properties, for their high hydrating capability and for their anti-hyaluronidase action.

As regards their antioxidant and anti-radical properties, they protect glycosaminoglycans (GAGs) from depolymerization by reactive oxygen species, as described in Moseley R et al., Biochim. Biophys. Acta., (1995), 1244(2-3), 245-52.

As regards their hydrating capability, for example R. Servaty et al., International Journal of Biological Macromolecules, (2001), 28, 121-127, demonstrated a greater absorption capability for water molecules by chondroitin sulphate, in comparison with hyaluronic acid, resulting from the presence of the sulphate group carried by chondroitin sulphate.

As regards their anti-hyaluronidase action, sulphated polysaccharides, and more particularly entirely O-sulphated glycosaminoglycans, are known for exhibiting high anti-hyaluronidase activity, for example from T. Toida et al., Archives of Biochemistry and Biophysics, 1999, 370(2), 176-182. The entirely O-sulphated glycosaminoglycans described in this publication are chondroitin sulphate, dermatan sulphate, heparin sulphate and sulphated hyaluronic acid. The results obtained show that all the entirely O-sulphated glycosaminoglycans inhibit hyaluronidases in a dose-dependent manner and that entirely O-sulphated hyaluronic acid is the best inhibitor of hyaluronidases among the entirely O-sulphated glycosaminoglycans tested. The disadvantage of the entirely O-sulphated hyaluronic acid is that it cannot be crosslinked.

However, in the field of aesthetics, more than 80% of compositions are based on crosslinked hyaluronic acid; it is thus not possible to develop a filler product based on non-crosslinked hyaluronic acid.

It might be possible to envisage the incorporation of a small amount of sulphated polysaccharide of animal origin in a composition based on hyaluronic acid; for example, Patent Application WO 03/041724 in the name of Hermida describes sterile injectable compositions based on a mixture of sodium hyaluronate and chondroitin sulphate intended for intra-articular use.

Likewise, in Patent Application WO 2004/034980 in the name of Marcum, injectable compositions based on hyaluronic acid, chondroitin sulphate and N-acetylglucosamine, for the regeneration of cartilage by intra-articular injection are described.

The disadvantage of such compositions remains the animal origin of chondroitin sulphate.

As regards sulphated polysaccharides of synthetic origin, tests on the inhibition of hyaluronidases in hyaluronic acid compositions by dextran sulphate have also been described, for example by K. Zimmermann, J. Cancer Res. Clin. Oncol., 1983, 105, pp 189-190. The hydrolysis of hyaluronic acid according to the Nelson method was measured for compositions comprising hyaluronic acid, hyaluronidases and also dextran sulphate with a molecular weight of 17.7 kDa at different concentrations. Dextran sulphate is described as a powerful inhibitor of hyaluronidases and, if the active doses for a dextran sulphate with a molecular weight of 17.7 kDa are far below toxic doses, toxicity increases with increasing molecular weight and only a few molecules of high molecular weight greatly increase toxicity, as has been demonstrated by Walton, Br. J. Pharmacol., 1954, 9, 1-14. Furthermore, dextran sulphate is described as being an anticoagulant which can be used in vivo and in vitro, as is described, for example, in U.S. Pat. No. 2,715,091, and these anticoagulant properties are a priori incompatible with uses as an ingredient of compositions which are implantable.

Among sulphated polysaccharides of plant origin, carrageenans are known, but these are known to bring about inflammatory reactions, so much so that models for testing anti-inflammatories are based on their properties.

In addition, WO 03/000191, in the name of Depuy, discloses compositions for the treatment of arthritic joints comprising hyaluronic acid and a hyaluronidase inhibitor, such as, for example, a sulphated polysaccharide, such as dextran sulphate, xylose sulphate or heparan sulphate, a portion of the components of which is encapsulated in liposomes in order to ensure the controlled diffusion thereof, but the use of liposomes in compositions intended in particular to be crosslinked seems difficult to envisage.

Thus, the majority of the polysaccharides which might be used as additives with hyaluronic acid in order to reduce the action of hyaluronidases are either of animal origin or exhibit potential toxicity, these two conditions being incompatible with the uses envisaged.

From a theoretical viewpoint, the incorporation of sulphates in a solution in the form of sulphate ions might be envisaged; however, their diffusion within the injected tissue would be much too fast, indeed even immediate, and thus ineffective for the anti-hyaluronidase properties of compositions in the field of dermal fillers or viscosupplementation. It is thus preferable to choose compounds functionalized by sulphate groups.

Another potential solution is the use of sulphated compounds belonging to the subfamilies of sulphated monosaccharides and sulphated oligosaccharides.

This subfamily of sulphated mono- or oligosaccharides (formed from 1 to 10 monosaccharide units) is interesting, as they can be made readily available by synthesis and, as their carbohydrate structure is nonetheless close to that of the constituent glycosaminoglycans of the ExtraCellular Matrix, they are very well metabolized whilst generating at the same time non-toxic decomposition products.

For example, galacto-oligosaccharides which are active with regard to hyaluronidases have been described in the works published by S. Salmen et al., Planta Medica, 71, No. 8, 2005, 727-732, in particular verbascose, planteose and neomycin, which exhibit anti-hyaluronidase activities which are from 100 to 500 times higher than that of apigenin, which is a known hyaluronidase inhibitor.

The anti-hyaluronidase properties of entirely O-sulphated oligosaccharides originating from hyaluronic acid are also described in the prior art, such as A. Suzuki et al., Glycobiology, 2001, 11(1), pp. 57-64. A correlation between the inhibition of hyaluronidases by O-sulphated oligosaccharides originating from hyaluronic acid, their degree of functionalization by sulphate groups and their size has been demonstrated. It is more particularly noted that the inhibitory activity of these O-sulphated oligosaccharides is related to their size.

There are also sulphated monosaccharides, such as sulphated glucosamines, such as, for example, glucosamine-3-sulphate, described as an inhibitor of cartilage decomposition by J. I. Fenton et al., *Osteoarthritis and Cartilage*, Volume 8, Issue 6, 2000, 444-451.

Among the oligosaccharides, there is also include, formed by the condensation of 2 monosaccharide units, a glucose and a fructose.

This sucrose, in the sulphated form, like other sulphated oligosaccharides, is described as being used as a topically applied would healing promoter, in solution or in collagenic matrices or based on polyvinyl alcohol in Patent EP 0 230 023 in the name of Marion Laboratories.

In WO 89/05646 and EP 0 640 346, in the name of Bar-Shalom, compositions comprising salts of sucrose octasulphate and more particularly examples with the aluminium salt of sucrose octasulphate, which is an insoluble salt intended for topical applications or injections into tissues, including joints, are described. The salts of sucrose octasulphate are used more particularly for their healing properties. In the context of the healing application, hyaluronic acid can also be used as an active agent which promotes healing.

WO 98/22114, in the name of Dumex-Alpharma, discloses compositions comprising compounds formed between a polysaccharide, such as chitosan or hyaluronic acid, and a sulphated oligosaccharide, such as sucrose octasulphate or one of its salts. These compositions, here again, are intended to promote healing of wounds in tissues comprising collagen, such as the skin, bones and mucous membranes. The formation of the complex is demonstrated by various techniques, such as, for example, NMR spectroscopy, infrared spectroscopy, X-ray diffraction, thermal analysis and tests of solubility under defined conditions.

The manufacture of compositions intended to be implanted or injected implies that the latter be sterilized during their manufacturing process, in order to observe the minimum sanitary requirements for such compositions. The most widely used sterilization method in processes for the manufacture of such compositions is steam sterilization or autoclaving and such a method can cause decomposition of the products making up the compositions. It is therefore essential that rheological, pH meter and biocompatibility properties be retained and preserved during autoclaving. The same applies with regard to the requirements for injectability through fine needles, which is their main mode of use.

It has been demonstrated, through tests in an entirely surprising and unexpected manner, that hyaluronic acid gels formulated with the water-soluble salts of sucrose octasulphate (SOS) are, among all the possible candidates, the only ones which make it possible to obtain compositions which are stable during steam sterilization, otherwise known as autoclaving, and that the latter additionally exhibit increased remanence due to their resistance to decomposition by hyaluronidases, in comparison with the gels comprising hyaluronic acid without a water-soluble salt of sucrose octasulphate.

The water-soluble salt of sucrose octasulphate has 8 sulphate groups per sucrose molecule; thus, in the gel formulated with water-soluble salt of sucrose octasulphate, the amount of sulphates added per mg of SOS is high. The Applicant Company has also demonstrated, just as surprisingly, that the addition of water-soluble salt of sucrose octasulphate to gels based on hyaluronic acid does not result in a fall in viscosity or elasticity of the gel during the sterilization.

In the present invention, the Applicant Company intends to solve the problem of degradation of compositions comprising hyaluronic acid by hyaluronidases through the addition of a water-soluble salt of sucrose octasulphate, while retaining the ability of these compositions to be used in the field of dermal fillers, viscosupplementation, cosmetic formulations or pharmaceutical formulations due to the stability of their rheological properties during the steam sterilization phase in the manufacturing process.

The present invention makes it possible to solve all of the abovementioned problems and in addition makes it possible to obtain compositions according to the invention which retain their rheological properties during autoclaving and which have a greater remanence (greater half life), in comparison with the compositions of the prior art.

The present invention relates to a sterilized composition comprising at least one crosslinked or non-crosslinked hyaluronic acid, or one of its salts, and at least one water-soluble salt of sucrose octasulphate, to the processes for the manufacture of said composition and to the use of said composition for the formulation of a viscosupplementation composition or for the formulation of a composition as a dermal filler, for the formulation of a cosmetic composition or for the formulation of a pharmaceutical composition.

The composition according to the invention has hyaluronidase resistant properties and is characterized by rheological properties which are retained after steam sterilization and which are at least similar to those of a composition comprising only at least one crosslinked or non-crosslinked hyaluronic acid, or one of its salts. The present invention also relates to a cosmetic formulation comprising the composition according to the invention and at least one cosmetically acceptable excipient.

Surprisingly, the present invention makes it possible to obtain compositions which are resistant to hyaluronidases and which meet the requirements of stability with regard to autoclaving of the compositions intended for the abovementioned fields.

The present invention relates to a composition, in an aqueous medium, comprising at least one hyaluronic acid and at least one water-soluble salt of sucrose octasulphate, characterized in that said composition is a physical mixture and in that the ratio by weight of the content of hyaluronic acid [HA] to the content of water-soluble salt of sucrose octasulphate [SOS], [HA]/[SOS], is greater than or equal to 0.1.

"Hyaluronic acid" is understood to mean crosslinked or non-crosslinked hyaluronic acid, alone or as a mixture, optionally chemically modified by substitution, alone or as a mixture, optionally in the form of one of its salts, alone or as a mixture.

In one embodiment, the composition according to the invention comprises at least one non-crosslinked hyaluronic acid or one of its salts, alone or as a mixture.

In one embodiment, the composition according to the invention comprises at least one crosslinked hyaluronic acid or one of its salts, alone or as a mixture.

In one embodiment, the composition according to the invention comprises at least one co-crosslinked hyaluronic acid or one of its salts, alone or as a mixture.

In one embodiment, the composition according to the invention comprises at least one crosslinked or non-crosslinked hyaluronic acid chemically modified by substitution or one of its salts, alone or as a mixture.

In one embodiment, the hyaluronic acid is in the sodium or potassium salt form.

In one embodiment, the composition according to the invention is characterized in that the water-soluble salt of sucrose octasulphate is chosen from the group consisting of alkali metal salts, alkaline earth metal salts, silver salts, ammonium salts and amino acid salts.

In one embodiment, the composition according to the invention is characterized in that the water-soluble salt of sucrose octasulphate is chosen from the group consisting of the alkali metal salts and the alkaline earth metal salts.

In one embodiment, the composition according to the invention is characterized in that the water-soluble salt of sucrose octasulphate is the sodium salt of sucrose octasulphate or the potassium salt of sucrose octasulphate.

In one embodiment, the composition according to the invention is characterized in that the water-soluble salt of sucrose octasulphate is the sodium salt of sucrose octasulphate.

In one embodiment, the composition according to the invention is characterized in that the water-soluble salt of sucrose octasulphate is the potassium salt of sucrose octasulphate.

The maximum solubility of the potassium salt of sucrose octasulphate is 40 mg/g; thus, the minimum [HA]/[SOS] ratio in the compositions of the present invention is 0.1, given that the minimum acceptable concentration of HA in the compositions of the present invention is 4 mg/g in order to obtain appropriate consistency for the uses of the present invention. As the solubility of the sodium salt of sucrose octasulphate is greater than that of the potassium salt, the solubility limit of the potassium salt of sucrose octasulphate has been taken into consideration in determining the minimum value of the [HA]/[SOS] ratio.

"Aqueous medium" is understood to mean a composition in the form of an aqueous solution, optionally in the presence of a soluble salt or a buffer, optionally in the form of gel or hydrogel.

"Physical mixture" is understood to mean a mixture in which all of the physicochemical properties of the mixture's constituents are retained, that is to say that they are strictly identical to those of the constituents of the mixture, taken separately, it being possible for the integrity of the physicochemical properties to be characterized by various analytical methods. The Applicant Company has chosen nuclear magnetic resonance (NMR) spectroscopy for characterizing the physical mixture. The NMR spectrum of the mixture according to the invention is a one-dimensional proton $^1$H spectrum. For example, the NMR spectrum of a physical mixture comprising a water-soluble salt of sucrose octasulphate is characterized in that the values of the chemical shifts of the protons of the water-soluble salt of sucrose octasulphate in solution, alone, are equal to the values of the chemical shifts of the protons of the water-soluble salt of sucrose octasulphate in the physical mixture according to the invention, which proves that there is no interaction or reaction between the water-soluble salt of sucrose octasulphate and the hyaluronic acid.

In one embodiment, the composition according to the invention is characterized in that, when it is analysed by proton $^1$H NMR spectroscopy, the value of the chemical shift of the anomeric proton ($\delta$=5.7 ppm) of the salt of sucrose octasulphate is identical to the value of the chemical shift of the anomeric proton of the salt of sucrose octasulphate alone in solution.

In one embodiment, the composition according to the invention is characterized in that the ratio by weight of the content of hyaluronic acid [HA] to the content of water-soluble salt of sucrose octasulphate [SOS], [HA]/[SOS], is comprised between 0.1 and 5000.

In one embodiment, the composition according to the invention is characterized in that the ratio by weight of the content of hyaluronic acid [HA] to the content of water-soluble salt of sucrose octasulphate [SOS], [HA]/[SOS], is comprised between 0.1 and 2500.

In one embodiment, the composition according to the invention is characterized in that the ratio by weight of the content of hyaluronic acid [HA] to the content of water-soluble salt of sucrose octasulphate [SOS], [HA]/[SOS], is comprised between 1 and 1000.

In one embodiment, the composition according to the invention is characterized in that the ratio by weight of the content of hyaluronic acid [HA] to the content of water-soluble salt of sucrose octasulphate [SOS], [HA]/[SOS], is comprised between 10 and 500.

In one embodiment, the composition according to the invention is characterized in that the ratio by weight of the content of hyaluronic acid [HA] to the content of water-soluble salt of sucrose octasulphate [SOS], [HA]/[SOS], is comprised between 0.1 and 100.

In one embodiment, the composition according to the invention is characterized in that the ratio by weight of the content of hyaluronic acid [HA] to the content of water-soluble salt of sucrose octasulphate [SOS], [HA]/[SOS], is comprised between 0.5 and 50.

In one embodiment, the composition according to the invention is characterized in that the ratio by weight of the content of hyaluronic acid [HA] to the content of water-soluble salt of sucrose octasulphate [SOS], [HA]/[SOS], is equal to 20.

In one embodiment, the composition according to the invention is characterized in that the content of water-soluble salt of sucrose octasulphate is comprised between 0.01 mg/g and 40 mg/g of composition.

In one embodiment, the composition according to the invention is characterized in that the content of water-soluble salt of sucrose octasulphate is comprised between 0.1 mg/g and 10 mg/g of composition.

In one embodiment, the composition according to the invention is characterized in that the content of water-soluble salt of sucrose octasulphate is comprised between 0.1 mg/g and 1 mg/g of composition.

In one embodiment, the composition according to the invention is characterized in that the content of hyaluronic acid is comprised between 2 mg/g and 50 mg/g of composition.

In one embodiment, the composition according to the invention is characterized in that the content of hyaluronic acid is comprised between 4 mg/g and 40 mg/g of composition.

In one embodiment, the composition according to the invention is characterized in that the content of hyaluronic acid is comprised between 10 mg/g and 30 mg/g of composition.

In one embodiment, the composition according to the invention is characterized in that it comprises at least one non-crosslinked hyaluronic acid.

In one embodiment, the composition according to the invention is characterized in that it comprises at least one crosslinked hyaluronic acid.

In the present invention, the degree of crosslinking X is defined as being equal to the ratio:

$$X = \frac{\left(\begin{array}{c}\text{Number of moles of crosslinking agent}\\ \text{introduced into the reaction medium}\end{array}\right)}{\left(\begin{array}{c}\text{Number of moles of disaccharide units}\\ \text{introduced into the reaction medium}\end{array}\right)}$$

In one embodiment, the crosslinked hyaluronic acid exhibits a degree of crosslinking X comprised between 0.001 and 0.5.

In one embodiment, the crosslinked hyaluronic acid exhibits a degree of crosslinking X comprised between 0.01 and 0.25.

In one embodiment, the crosslinked hyaluronic acid exhibits a degree of crosslinking X comprised between 0.1 and 0.2.

In one embodiment, the hyaluronic acid is co-crosslinked as described in Application WO 2000/0046253 in the name of Fermentech or WO 2004/092222 in the name of Corneal or even FR 2 865 737 in the name of Anteis.

In one embodiment, the composition according to the invention is characterized in that it comprises a mixture of crosslinked and non-crosslinked hyaluronic acids as described in Application WO 2005/061611 in the name of Innomed Ltd.

In one embodiment, the composition according to the invention is characterized in that it comprises a mixture of crosslinked hyaluronic acids.

In one embodiment, the mixture of crosslinked hyaluronic acids is a single-phase mixture, such as that described in Patent Application WO 2009/071697 in the name of the Applicant Company.

In one embodiment, the composition according to the invention is characterized in that it comprises at least one hyaluronic acid substituted by a group contributing lipophilic or hydrophilic properties, such as, for example, the substituted hyaluronic acids as described in Application WO 2013/079889 in the name of the Applicant Company.

In one embodiment, the composition additionally comprises another polysaccharide.

In one embodiment, this other polysaccharide is chosen from the group consisting of cellulose, alginic acid or one of their salts.

Mw or "molecular weight" refers to the weight-average molecular weight of the polymers, measured in daltons.

In one embodiment, the composition according to the invention is characterized in that the molecular weight Mw of the hyaluronic acid is comprised within a range from 0.01 MDa to 5 MDa.

In one embodiment, the composition according to the invention is characterized in that the molecular weight Mw of the hyaluronic acid is comprised within a range from 0.1 MDa to 3.5 MDa.

In one embodiment, the composition according to the invention is characterized in that it additionally comprises at least one active principle.

In one embodiment, the composition according to the invention is characterized in that the active principle is chosen from antioxidants, local anaesthetics or vitamins, alone or combination.

In one embodiment, the composition according to the invention is characterized in that the antioxidants are chosen from polyols.

In one embodiment, the composition according to the invention is characterized in that the antioxidants are chosen from mannitol and sorbitol, alone or in combination.

In one embodiment, the composition according to the invention is characterized in that the antioxidant is mannitol.

In one embodiment, the composition according to the invention is characterized in that the antioxidant is sorbitol.

In one embodiment, the composition according to the invention is characterized in that the antioxidant is a combination of mannitol and sorbitol.

In one embodiment, the composition according to the invention is characterized in that the local anaesthetics are chosen from the group consisting of lidocaine, procaine, mepivacaine, ropivacaine, bupivacaine and their pharmaceutically acceptable salts.

In one embodiment, the composition according to the invention is characterized in that the local anaesthetic is lidocaine hydrochloride.

In one embodiment, the composition according to the invention is characterized in that the content of active principle(s) is comprised between 0.01 and 10% by weight, with respect to the total weight of the composition.

In one embodiment, the composition according to the invention is characterized in that the content of active principle(s) is comprised between 0.1 and 5% by weight, with respect to the total weight of the composition.

In one embodiment, the composition according to the invention is characterized in that it is stable to sterilization by steam autoclaving.

In one embodiment, the invention is a viscosupplementation composition, characterized in that it comprises at least one composition according to the invention.

In one embodiment, the invention is a composition for the treatment of xerophthalmia or ocular dryness, characterized in that it comprises at least one composition according to the invention.

Said compositions are used as artificial tears, tear gels or lubricants, dependent on the embodiment.

In one embodiment, the invention is a cosmetic formulation, characterized in that it comprises a composition according to the invention and at least one cosmetically acceptable excipient.

In one embodiment, the cosmetic formulation according to the invention is characterized in that it comprises between 0.01 and 10% by weight of a composition according to the invention, with respect to the total weight of the said cosmetic formulation.

In one embodiment, the cosmetic formulation according to the invention is characterized in that the at least one cosmetically acceptable excipient is chosen from conventional cosmetic adjuvants.

"Conventional cosmetic adjuvants" is understood to mean excipients chosen in particular from fatty substances, organic solvents, ionic or non-ionic thickeners, softeners, antioxidants, opacifying agents, stabilizing agents, emollients, silicones, α-hydroxy acids, antifoaming agents, moisturizing agents, fragrances, preservatives, surfactants, fillers, sequestering agents, polymers, propellants, basifying or acidifying agents, colorants or any other ingredient normally used in cosmetics.

The cosmetic formulation according to the invention can additionally comprise other active agents, in particular moisturizing agents, humectants, soothing agents, anti-inflammatories or healing agents.

The cosmetic formulations according to the invention can be prepared according to techniques well known to a person skilled in the art, in particular those intended for the preparation of emulsions of Oil-in-Water (O/W) or Water-in-Oil (W/O) type.

This cosmetic formulation can be provided in particular in the form of a simple or complex (O/W, W/O, O/W/O or W/O/W) emulsion, such as a cream, a milk, a gel or a cream gel, of a powder or of a solid stick and can optionally be packaged in an aerosol and be provided in the form of a mousse or spray.

In one embodiment, the cosmetic formulation is sterilized according to the techniques well known to a person skilled in the art and in particular by gamma irradiation.

The present invention also relates to a cosmetic formulation according to the invention, characterized in that it can be administered by topical administration in the form of a lotion, cream, oil, stick, shampoo or any other appropriate form.

The cosmetic, dermatological or pharmaceutical formulation according to the invention can be used as composition for protecting the human epidermis against attacks by external factors and can thus combat premature ageing of the epidermis.

The invention also relates to a process for the manufacture of a composition according to the invention.

In one embodiment, the process according to the invention is characterized in that it comprises at least:

a hydration step of fibres of at least one hyaluronic acid, in order to obtain a hydrogel, a mixing step of a solution of water-soluble salt of sucrose octasulphate with the hydrogel obtained in the preceding step, a homogenization step, and a steam autoclaving step.

In one embodiment, the process according to the invention is characterized in that the hydration step is carried out at ambient temperature.

In one embodiment, the process according to the invention is characterized in that the homogenization step is carried out at ambient temperature.

In one embodiment, the process according to the invention is characterized in that the steam autoclaving step is carried out at a temperature of 121 to 134° C., for a period of time adjusted to the temperature.

In one embodiment, the process according to the invention is characterized in that it additionally comprises at least one packaging step in which the homogenized mixture is packaged into syringes.

In one embodiment, the process according to the invention is characterized in that it additionally comprises at least one packaging step in which the homogenized mixture is packaged into single-dose bottles.

In one embodiment, the process according to the invention is characterized in that it additionally comprises at least one crosslinking step.

In one embodiment, the process according to the invention is characterized in that the crosslinking step is carried out between the hydration step and the mixing step.

In one embodiment, the process according to the invention is characterized in that it comprises a step of mixing two previously crosslinked hyaluronic acids as in the process described in WO 2013/079889.

In one embodiment, the process according to the invention is characterized in that the crosslinking step is carried out by means of at least one crosslinking agent.

In one embodiment, the process according to the invention is characterized in that the crosslinking agent is bi- or polyfunctional.

In one embodiment, the process according to the invention is characterized in that the bi- or polyfunctional crosslinking agent is chosen from the group consisting of ethylene glycol didiglycidyl ether, butanediol diglycidyl ether (BDDE), polyglycerol polyglycidyl ether, polyethylene glycol diglycidyl ether, polypropylene glycol diglycidyl ether, a bis- or polyepoxy, such as 1,2,3,4-diepoxybutane or 1,2,7,8-diepoxyoctane, a dialkyl sulphone, divinyl sulphone, formaldehyde, epichlorohydrin or alternatively glutaraldehyde, or carbodiimides, such as, for example, 1-ethyl-3-[3-dimethylaminopropyl]carbodiimide hydrochloride (EDC).

In one embodiment, the process according to the invention is characterized in that the bifunctional crosslinking agent is butanediol diglycidyl ether (BDDE) or 1,2,7,8-diepoxyoctane.

In one embodiment, the manufacturing process according to the invention is characterized in that the crosslinking step is carried out according to techniques known to a person skilled in the art.

In one embodiment, the process according to the invention is characterized in that it comprises, after the crosslinking step, at least one purification and washing step carried out according to techniques known to a person skilled in the art.

The invention relates to the use of a composition according to the invention for the formulation of a viscosupplementation composition.

The invention relates to the use of a composition according to the invention for the formulation of a composition as a dermal filler.

The applications targeted are more particularly those commonly observed in the context of injectable viscoelastic products and polysaccharides used or potentially usable in the following pathologies or treatments:

aesthetic injections in the face: for dermal filling, skin defects or defects of volume (cheekbones, chin, lips);

volumizing injections in the body: breast and buttock enhancement, enhancement of the G spot, vaginoplasty, reconstruction of the vaginal labia or penis enlargement;

treatment of osteoarthritis, injection into the joint to replace or supplement deficient synovial fluid;

periurethral injection in the treatment of urinary incontinence due to sphincter insufficiency;

postsurgical injection for preventing peritoneal adhesions in particular;

injection subsequent to surgery for long-sightedness due to scleral incisions using a laser;

injection into the vitreous cavity.

More particularly, in aesthetic surgery, according to its viscoelastic properties and properties of remanence, the hydrogel obtained according to the process of the invention can be used:

for filling in fine, moderate or deep wrinkles and can be injected with thin needles (27-gauge, for example);

as volumizing product with injection via needles with a larger diameter, for example from 22- to 26-gauge, and with a greater length (30 to 40 mm, for example); in this case, its cohesive nature will make it possible to guarantee that it is maintained at the site of the injection.

The composition according to the invention also has an important application in joint surgery and in dental surgery for filling in periodontal pockets, for example.

These implementational examples are in no way limiting, the composition according to the present invention being more widely provided for:

filling in volumes;

generating spaces within certain tissues, thus promoting their optimum functioning;

replacing deficient physiological fluids.

The invention also relates to a kit comprising a composition according to the invention, packaged in syringes and sterilized after packaging.

The invention also relates to a kit comprising a composition according to the invention, packaged in single-dose bottles and sterilized after packaging.

The composition according to the invention is also useful in the cosmetics or pharmaceutical field.

More particularly, in the cosmetics field, a composition according to the invention will be used as moisturizing active ingredient in a cosmetic composition.

In the pharmaceutical field, a composition according to the invention will be used as composition for hydrating eyes affected by ocular dryness, namely as artificial tears.

In these cosmetic and/or pharmaceutical applications, the compositions can additionally comprise any cosmetically or pharmaceutically acceptable ingredient.

The characteristics of the composition according to the present invention and also the processes for its manufacture and their properties are illustrated in the examples below.

EXAMPLE 1

This example illustrates a composition according to the invention comprising non-crosslinked hyaluronic acid and potassium sucrose octasulphate.

Injectable grade, sodium hyaluronate (NaHA) fibres (1 g; molecular weight: approximately 2.7 MDa) are weighed in a container. An aqueous solution of phosphate buffer (32.3 g) is added and everything is homogenized for approximately 1 hour using a spatula, at ambient temperature and under an atmospheric pressure of 900 mmHg.

The non-crosslinked NaHA hydrogel thus obtained has an NaHA concentration of approximately 30 mg/g.

Potassium sucrose octasulphate (KSOS) (60 mg, i.e. 4.7× $10^{-5}$ mol) is dissolved in a solution of phosphate buffer (19.94 g) in order to obtain an aqueous solution of potassium sucrose octasulphate with a concentration of 3 mg/g.

The NaHA hydrogel obtained in the preceding step is diluted by addition of the aqueous solution of potassium sucrose octasulphate prepared above. The composition thus obtained is subsequently homogenized.

A composition is thus obtained comprising non-crosslinked NaHA at a concentration of 20 mg/g and KSOS at a concentration of 1 mg/g; the [HA]/[SOS] ratio by weight is thus 20.

The composition thus obtained is packaged in syringes, which are sterilized by steam autoclaving (T=121° C., 10 min).

The gels described in Table 7 are prepared according to a procedure identical to that described above, by adjusting the amounts employed.

EXAMPLE 2

This example illustrates an example of a composition according to the invention comprising crosslinked hyaluronic acid and potassium sucrose octasulphate.

The composition comprising crosslinked hyaluronic acid is obtained according to the crosslinking procedure described in WO 2009/071697 (Example 1, first part) in the name of Vivacy starting from sodium hyaluronate (NaHA) fibres (1 g; molecular weight: approximately 2.7 MDa) and butanediol diglycidyl ether (BDDE) (54 mg). The composition thus obtained has a concentration of crosslinked NaHA of approximately 30 mg/g, with a degree of crosslinking X of approximately 0.12.

An aqueous solution of potassium sucrose octasulphate with a concentration of 3 mg/g is prepared as in Example 1.

The crosslinked NaHA hydrogel obtained in the preceding step is diluted in the aqueous solution of potassium sucrose octasulphate prepared above. The composition thus obtained is subsequently homogenized.

A composition is thus obtained which comprises crosslinked NaHA at a concentration of 20 mg/g and potassium sucrose octasulphate at a concentration of 1 mg/g; the [HA]/[SOS] ratio by weight is thus 20.

The composition thus obtained is packaged in syringes, which are sterilized by steam autoclaving (T=121° C., 10 min).

The gel described in Table 8 is prepared according to a procedure identical to that described above, by adjusting the amounts employed.

EXAMPLE 3

This example illustrates an example of a composition according to the invention comprising a non-crosslinked hyaluronic acid, potassium sucrose octasulphate and mannitol.

The composition comprising non-crosslinked hyaluronic acid and potassium sucrose octasulphate is prepared according to the procedure of Example 1, starting from a hyaluronic acid hydrogel at a concentration of 30 mg/g and a solution of potassium sucrose octasulphate at a concentration of 10 mg/g.

The addition of a solution of mannitol at a concentration of 86 mg/g to the composition obtained above is carried out according to the procedure described in WO 2009/024670 in the name of Anteis.

The composition thus obtained comprises non-crosslinked hyaluronic acid at a concentration of 20 mg/g, mannitol at a concentration of 20 mg/g and potassium sucrose octasulphate at a concentration of 1 mg/g; the [HA]/[SOS] ratio by weight is thus 20.

The composition thus obtained is packaged in syringes, which are sterilized by steam autoclaving (T=121° C., 10 min).

EXAMPLE 4

This example illustrates an example of a composition according to the invention comprising crosslinked hyaluronic acid, potassium sucrose octasulphate and mannitol.

The composition comprising crosslinked NaHA is prepared according to the procedure described in Example 2, starting from an NaHA hydrogel at a concentration of 30 mg/g and potassium sucrose octasulphate at a concentration of 10 mg/g.

The addition of a solution of mannitol at a concentration of 86 mg/g to the composition obtained above is carried out according to the procedure described in WO 2009/024670 in the name of Anteis.

The composition thus obtained comprises crosslinked hyaluronic acid at a concentration of 20 mg/g, mannitol at a concentration of 20 mg/g and potassium sucrose octasulphate at a concentration of 1 mg/g; the [HA]/[SOS] ratio by weight is thus 20.

The composition thus obtained is packaged in syringes, which are sterilized by steam autoclaving (T=121° C., 10 min).

EXAMPLE 5

This example illustrates an example of a composition according to the invention comprising non-crosslinked hyaluronic acid, potassium sucrose octasulphate and lidocaine.

The composition comprising non-crosslinked hyaluronic acid and potassium sucrose octasulphate is prepared according to the procedure of Example 1, starting from a hyaluronic acid hydrogel at a concentration of 30 mg/g and a solution of potassium sucrose octasulphate at a concentration of 10 mg/g.

The addition of a lidocaine solution at a concentration of 13 mg/g to the composition obtained above is carried out according to the procedure described in WO 2009/024670 in the name of Anteis or according to the procedure described in Applications U.S. 61/791,977 or FR 13/52971 in the name of Vivacy.

The composition thus obtained comprises non-crosslinked hyaluronic acid at a concentration of 20 mg/g, lidocaine at a concentration of 3 mg/g and potassium sucrose octasulphate at a concentration of 1 mg/g; the [HA]/[SOS] ratio by weight is thus 20.

The composition thus obtained is packaged in syringes, which are sterilized by steam autoclaving (T=121° C., 10 min).

EXAMPLE 6

This example illustrates an example of a composition according to the invention comprising crosslinked hyaluronic acid, potassium sucrose octasulphate and lidocaine.

A composition comprising crosslinked NaHA is prepared according to the procedure described in Example 2, starting from NaHA hydrogel at a concentration of 30 mg/g and potassium sucrose octasulphate at a concentration of 10 mg/g.

The addition of a solution of lidocaine at a concentration of 13 mg/g to the composition obtained above is carried out according to the procedure described in WO 2009/024670 in the name of Anteis or according to the procedure described in Application U.S. 61/791,977 or FR 13/52971 in the name of Vivacy.

The composition thus obtained comprises crosslinked hyaluronic acid at a concentration of 20 mg/g, lidocaine at a concentration of 3 mg/g and potassium sucrose octasulphate at a concentration of 1 mg/g; the [HA]/[SOS] ratio by weight is thus 20.

The composition thus obtained is packaged in syringes, which are sterilized by steam autoclaving (T=121° C., 10 min).

The compositions obtained in Examples 1 to 6 can be used in viscosupplementation or as a filler fluid.

EXAMPLE 7

This example illustrates a composition according to the invention comprising non-crosslinked hyaluronic acid and potassium sucrose octasulphate for the treatment of ocular dryness.

Injectable grade, sodium hyaluronate (NaHA) fibres (1 g; molecular weight: approximately 1 MDa) are weighed in a container. An aqueous solution of phosphate buffer (165.7 g) is added and everything is homogenized for approximately 1 hour using a spatula, at ambient temperature and under an atmospheric pressure of 900 mmHg.

The non-crosslinked NaHA hydrogel thus obtained has an NaHA concentration of approximately 6 mg/g.

Potassium sucrose octasulphate (KSOS) (600 mg, i.e. $4.7 \times 10^{-4}$ mol) is dissolved in a solution of phosphate buffer (19.94 g) in order to obtain an aqueous solution of potassium sucrose octasulphate with a concentration of 30 mg/g.

The NaHA hydrogel obtained in the preceding stage is diluted by addition of the aqueous solution of potassium sucrose octasulphate prepared above. The composition thus obtained is subsequently homogenized.

A composition is thus obtained which comprises non-crosslinked NaHA at a concentration of 4 mg/g and KSOS at a concentration of 10 mg/g; the [HA]/[SOS] ratio by weight is thus 0.4.

The composition thus obtained is packaged in single-dose bottles, which are sterilized.

EXAMPLE 8

This example illustrates a cosmetic formulation.

| | |
|---|---|
| Cetearyl alcohol | 5% |
| Esters (dicaprylyl ether, myristyl myristate) | 10% |
| Non-crosslinked hyaluronic acid and potassium sucrose octasulphate composition obtained in Example 1 | 1% |
| Glycerol | 5% |
| Alcohol | 5% |
| Tocopherol | 0.2% |
| Fragrance | 0.1% |
| Water | q.s. for 100% |

EXAMPLE 9

This example illustrates a sterilized cosmetic formulation.

| | |
|---|---|
| Non-crosslinked hyaluronic acid and potassium sucrose octasulphate composition obtained according to Example 1 with an [HA]/[SOS] ratio of 4 | 1% |

| Carbomer | 0.5% |
|---|---|
| Xanthan gum | 2.5% |
| Citric acid | 0.1% |
| 2-Phenylethanol | 0.5% |
| Glycerol | 1.2% |
| Water | q.s. for 100% |

The cosmetic formulation is sterilized by gamma irradiation at doses of 5-25 kGy and preferably of 7-15 kGy.

EXAMPLE 10

Stability with Regard to Steam Autoclaving

For the compositions according to the invention comprising non-crosslinked hyaluronic acid, the viscosity η of the sterilized compositions after the steam autoclaving step is characterized on a TA Instruments AR 2000 Ex rheometer, under controlled constraint conditions, at 25° C. The viscosity value is recorded at a constraint of 0.02 s$^{-1}$.

For the compositions comprising non-crosslinked hyaluronic acid, the percentage of loss in the viscosity is the value of the difference in the viscosity of the reference composition after steam autoclaving and the viscosity of the composition comprising non-crosslinked hyaluronic acid and a sulphated oligo-polysaccharide or a sulphated monosaccharide after steam autoclaving over the value of the viscosity of the reference composition after steam autoclaving.

For the compositions according to the invention comprising crosslinked hyaluronic acid, the elastic component G' of the sterilized compositions after the autoclaving step is characterized on a TA Instruments AR 2000 Ex rheometer, under oscillation conditions, at 25° C., the values of the elastic component being recorded at a frequency of 1 Hz.

For the compositions comprising crosslinked hyaluronic acid, the percentage of loss in the elastic component G' is the value of the difference in the elastic component G' of the reference composition after steam autoclaving and the elastic component G' of the composition comprising crosslinked hyaluronic acid and a sulphated oligo-polysaccharide or a sulphated monosaccharide after steam autoclaving over the value of the elastic component G' of the reference composition after steam autoclaving.

For these all measurements, a reference composition is formulated, the aqueous solution of sulphated oligo-polysaccharide or of sulphated monosaccharide being replaced by the same amount of aqueous solution of phosphate buffer.

a) Stability with Regard to Steam Autoclaving of Compositions Comprising Non-Crosslinked Hyaluronic Acid and a Sulphated Oligo-Polysaccharide or a Sulphated Monosaccharide.

Nine compositions comprising non-crosslinked hyaluronic acid and a sulphated oligo-polysaccharide or a sulphated monosaccharide at a concentration of 1 mg/g in the composition are prepared according to the procedure described in Example 1.

A reference composition is also formulated, the aqueous solution of sulphated oligo-polysaccharide or of sulphated monosaccharide being replaced by the same amount of aqueous solution of phosphate buffer.

The percentages of loss in the viscosity of the compositions according to the procedure of Example 1, with respect to the reference composition after the steam autoclaving step, are measured and the results obtained are presented in Table 1 below:

TABLE 1

Percentage of loss in the viscosity after the steam autoclaving step of compositions comprising non-crosslinked hyaluronic acid and a sulphated oligo-polysaccharide or a sulphated monosaccharide at a concentration of 1 mg/g, with respect to the reference composition

| Sulphated oligo-polysaccharides and sulphated monosaccharides | % of loss in the viscosity with respect to the reference composition |
|---|---|
| N-Acetyl-D-glucosamine-6-sulphate | 96 |
| D-Glucosamine-6-sulphate | 98 |
| D-Glucosamine-2-sulphate | 87 |
| Dextran sulphate$_{(40000)}$ | 16 |
| Chondroitin sulphate | 62 |
| Disulphated carrageenan$_{(disaccharide)}$ | 94 |
| Hexasulphated carrageenan$_{(hexasaccharide)}$ | 92 |
| Sodium sucrose octasulphate | 0 |
| Potassium sucrose octasulphate | 0 |

After the steam autoclaving step, a loss in the viscosity is observed for all the compositions, with exception of those comprising a water-soluble salt of sucrose octasulphate. The greatest losses are observed for the compositions comprising sulphated glucosamines (N-acetylated or not and sulphated in the 2 or 6 position). As regards those comprising a sulphated oligo-polysaccharide, such as dextran sulphate or chondroitin sulphate, they appear smaller.

b) Stability Towards Steam Autoclaving of Compositions Comprising Non-Crosslinked Hyaluronic Acid, a Sulphated Oligo-Polysaccharide or a Sulphated Monosaccharide and Mannitol A series of five compositions comprising non-crosslinked hyaluronic acid, mannitol and a sulphated oligo-polysaccharide or a sulphated monosaccharide at a concentration of 1 mg/g in the composition is prepared according to the procedure described in Example 3.

A reference composition is also formulated, the aqueous solution of sulphated oligo-polysaccharide or of sulphated monosaccharide being replaced by the same amount of aqueous solution of phosphate buffer.

The percentages of loss in the viscosity of the compositions according to the procedure of Example 3, with respect to the reference composition, are measured and the results obtained are presented in Table 2 below:

TABLE 2

Percentage of loss in the viscosity after the steam autoclaving step of compositions comprising non-crosslinked hyaluronic acid, mannitol and a sulphated oligo-polysaccharide or a sulphated monosaccharide at a concentration of 1 mg/g, with respect to the reference composition

| Sulphated oligo-polysaccharides and sulphated monosaccharides | % of loss in the viscosity with respect to the reference composition |
|---|---|
| N-Acetyl-D-glucosamine-6-sulphate | 60 |
| D-Glucosamine-6-sulphate | 90 |
| D-Glucosamine-2-sulphate | 25 |
| Sodium sucrose octasulphate | 0 |
| Potassium sucrose octasulphate | 0 |

A loss in the viscosity, with respect to the reference composition, is observed for the compositions comprising non-crosslinked hyaluronic acid, mannitol and a glucosamine sulphate.

The only compositions for which no loss in the viscosity is observed after steam autoclaving, with respect to the reference composition, are the compositions comprising a water-soluble salt of sucrose octasulphate.

c) Stability Towards Steam Autoclaving of Compositions Comprising Crosslinked Hyaluronic Acid, a Sulphated Oligo-Polysaccharide or a Sulphated Monosaccharide and Mannitol A series of four compositions comprising crosslinked hyaluronic acid, mannitol and a sulphated oligo-polysaccharide or a sulphated monosaccharide at a concentration of 1 mg/g in the composition is prepared according to the procedure described in Example 4.

A reference composition is also formulated, the aqueous solution of sulphated oligo-polysaccharide or of sulphated monosaccharide being replaced by an equivalent amount of aqueous solution of phosphate buffer.

The percentages of loss in the elastic component G' of the compositions according to the procedure of Example 4, with respect to the reference composition, are measured and the results obtained are presented in Table 3 below:

TABLE 3

Percentage of loss in the elastic component G' after the steam autoclaving stage of compositions comprising crosslinked hyaluronic acid, mannitol and a sulphated oligo-polysaccharide or a sulphated monosaccharide at a concentration of 1 mg/g, with respect to the reference composition

| Sulphated oligo-polysaccharides and sulphated monosaccharides | % of loss in the elastic component G' with respect to the reference composition |
|---|---|
| N-Acetyl-D-glucosamine-6-sulphate | 32 |
| D-Glucosamine-6-sulphate | 74 |
| D-Glucosamine-2-sulphate | 18 |
| Potassium sucrose octasulphate | 0 |

Losses in the elastic component G', with respect to the reference composition, are observed for the compositions comprising sulphated glucosamines (N-acetylated or not and sulphated in the 2 or 6 position).

It is observed, for the compositions comprising potassium sucrose octasulphate, that there is no loss in the component G' after steam autoclaving, with respect to the reference composition.

In conclusion, no loss in the viscosity or in the elastic component G' is observed after steam autoclaving, with respect to the reference composition, only for the compositions comprising water-soluble sodium sucrose octasulphate or potassium sucrose octasulphate salts. This observation is the same whether or not the hyaluronic acid is crosslinked and whether or not the compositions comprise mannitol.

Consequently, these compositions are the only ones which make it possible to obtain products just as stable as the reference composition after steam autoclaving.

EXAMPLE 11

Spectroscopic Characteristics of the Physical Mixture Comprising Hyaluronic Acid and Potassium Sucrose Octasulphate A $^1$H NMR analysis was carried out on the composition of Example 4. Spectroscopic characterization was carried out on the composition of Example 4 before sterilization and after sterilization by steam autoclaving.

Solution analysis was carried out on a Bruker Avance spectrometer operating at 600 MHz ($^1$H) and equipped with a TCI probe (Cryo Probe).

Figure 2:
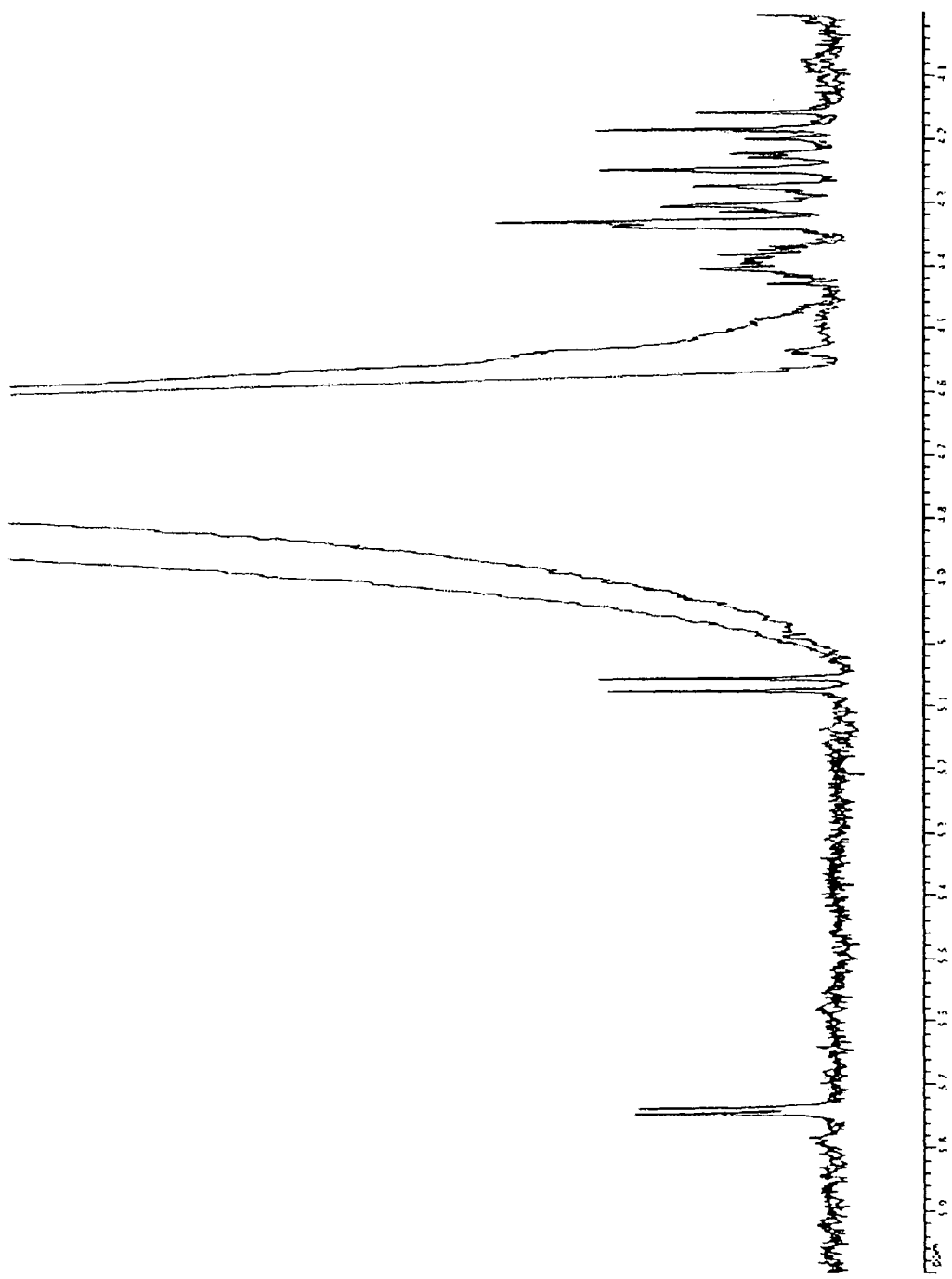

The results are presented below:

FIG. 1 is the $^1$H NMR spectrum of potassium sucrose octasulphate alone, in solution in water, FIG. 2 is a superimposition of the $^1$H NMR spectra of the composition of Example 4 before and after sterilization.

The $^1$H NMR spectrum of FIG. 1 of potassium sucrose octasulphate alone in solution in water made it possible to partially assign the signals. The value of the chemical shift of the anomeric proton of potassium sucrose octasulphate, which is $\delta=5.7$ ppm, is taken as reference.

Representation of the Anomeric Proton of Sucrose Octasulphate

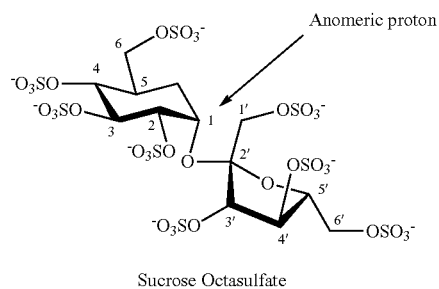

Sucrose Octasulfate

The values of the chemical shift of the anomeric proton of potassium sucrose octasulphate, alone in solution or in the composition of Example 4, are identical. Consequently, the NMR analysis confirms that potassium sucrose octasulphate does not react with hyaluronic acid to form a complex and that the composition of Example 4 is a physical mixture of an aqueous solution of potassium sucrose octasulphate and of the hydrogel comprising crosslinked hyaluronic acid.

The superimposition of the $^1$H NMR spectra of FIG. 2 of the composition of Example 4 before and after sterilization by steam autoclaving confirms the very great similarity of the two spectra. The chemical structures of potassium sucrose octasulphate and of hyaluronic acid are unchanged following sterilization by steam autoclaving, as illustrated in FIG. 2. This confirms the results relating to the rheological properties of the composition of Example 4 set out above.

EXAMPLE 12

Enzymatic Degradation Tests

The degradation test was developed on the basis of the test described in the publication "Comparison of the sensitivity of 11 crosslinked hyaluronic acid gels to bovine testis hyaluronidase", I. Sall and G. Ferard, Polymer Deg. and Stability, (2007), 92, 915-919, and Patent Application WO 2009/068215.

The enzymatic decomposition tests were carried out on a composition prepared according to the procedure of Example 2, comprising crosslinked NaHA at a concentration of 20 mg/g and potassium sucrose octasulphate at a concentration of 3 mg/g in NaCl buffer (composition A), and on the composition of Example 4 (composition B), which are sterilized by steam autoclaving, and on reference compositions, also sterilized by steam autoclaving. The reference composition A and the reference composition B are formulated by replacing the aqueous solution of potassium sucrose octasulphate by the same amount of aqueous solution of phosphate buffer.

The compositions were subjected to an in vitro enzymatic degradation test at 37° C. This test makes it possible to simulate the subsequent in vivo remanence of the injected compositions.

The said compositions are degraded by hyaluronidases on mixing the test compositions with a hyaluronidase solution.

The degradation is monitored by rheology at 37° C. (on a TA Instruments AR 2000 Ex rheometer), the complex viscosity being measured. The curves of the trend in the degradation results for these two compositions subsequently make it possible to evaluate the half-life of these various compositions (period of time necessary to have $n^*=n^*_0/2$, in minutes, with $n^*_0$=complex viscosity at $t_0$ of the composition characterized).

The half-lives obtained are given in Table 4 below:

TABLE 4

Enzymatic degradation tests on a composition according to Example 2 with a KSOS concentration of 3 mg/g (composition A) and on the composition of Example 4 (composition B), which are sterilized by steam autoclaving, and on reference compositions based on crosslinked hyaluronic acid, sterilized by steam autoclaving

| Composition | Enzymatic decomposition (Hyaluronidases) Half-life (min) |
|---|---|
| Reference composition A | 5.1 |
| Composition A | 6.3 |
| Reference composition B | 6.1 |
| Composition B | 8.7 |

Compositions A and B, which are sterilized by steam autoclaving, exhibit greater half-lives than those of the reference compositions, sterilized by steam autoclaving, under the same conditions; specifically, the compositions A and B, which are sterilized by steam autoclaving, respectively have remanences greater by 24% and 43% with regard to enzymatic degradation, with respect to the reference compositions A and B, which are sterilized by steam autoclaving.

EXAMPLE 13

Oxidative Degradation Tests

The oxidative degradation tests were carried out on the composition according to Example 4, sterilized by steam autoclaving, and on a reference composition, also sterilized by steam autoclaving, under the same conditions. The reference composition is formulated by replacing the aqueous solution of potassium sucrose octasulphate by the same amount of aqueous solution of phosphate buffer.

The compositions were subjected to an in vitro oxidative degradation test at 45° C. This test makes it possible to simulate the subsequent in vivo remanence of the injected compositions.

The compositions are degraded in the presence of aqueous hydrogen peroxide solution. The degradation is monitored by rheology at 45° C. (on a TA Instruments AR 2000 Ex rheometer), the complex viscosity being measured. The curves of the trend in the degradation results for these compositions subsequently make it possible to evaluate the half-life of these various compositions (period of time necessary to have $n^*=n^*_0/2$, in minutes, with $n^*_0$=complex viscosity at $t_0$ of the composition characterized).

The half-lives obtained are given in Table 5 below:

TABLE 5

Oxidative degradation tests on a composition of Example 4, sterilized by steam autoclaving, and on a reference composition based on crosslinked hyaluronic acid, sterilized by steam autoclaving

| Saccharides | Oxidative decomposition ($H_2O_2$) Half-life (min) |
|---|---|
| Reference composition | 19.95 |
| Potassium sucrose octasulphate | 25.85 |

The composition according to Example 4, sterilized by steam autoclaving, exhibits a greater half-life than that of the reference composition, sterilized by steam autoclaving, under the same conditions; specifically, the composition of Example 4, sterilized by steam autoclaving, has a remanence greater by 30% with regard to the oxidative degradation, with respect to the reference composition, sterilized by steam autoclaving.

EXAMPLE 14

Examples of tests on formulations of KSOS (at different concentrations) with a 20 mg/g crosslinked NaHA gel (IPN-like gel, sold under the Stylage® M brand), which is the reference gel.

The gels are sterilized and then characterized.

The percentage of loss in the elastic component G' with respect to the reference composition is measured according to Example 8 and the difference between the injectability force, through 30-gauge ½ hypodermic needles, of the reference gel and of the gels comprising potassium sucrose octasulphate is measured.

The results are presented in Table 6 below:

TABLE 6

Percentage of loss in the elastic component G' after the steam autoclaving step of compositions comprising crosslinked hyaluronic acid in the presence of variable concentrations of potassium sucrose octasulphate

| Stylage ® M Reference | % of loss in the elastic component G', with respect to the reference composition | $\Delta_{injectability\ force}$ (N) = Injectability force reference gel (N) − Injectability force gel with KSOS (N) | [HA]/ [SOS] |
|---|---|---|---|
| +3 mg/g KSOS | 0 | 0 | 6.66 |
| +1 mg/g KSOS | 0 | 0 | 20 |
| +0.5 mg/g KSOS | 0 | 0 | 40 |
| +0.2 mg/g KSOS | 0 | 0 | 100 |

No loss in the elastic component G' is observed after the autoclaving step of the compositions comprising crosslinked hyaluronic acid and potassium sucrose octasulphate, whatever the concentration of potassium sucrose octasulphate in the composition.

Neither is any increase in the injectability force observed, with respect to the reference formulation, whatever the potassium sucrose octasulphate content.

EXAMPLE 15

Examples of tests on formulations of KSOS (at different concentrations) with a non-crosslinked gel of Example 1 at the concentrations and ratios described in Table 7 below.

The gels are sterilized and then characterized by rheology according to Example 8.

TABLE 7

Percentage of loss in the viscosity after the autoclaving stage of compositions at different [HA]/[SOS] ratios

| NaHA concentration (mg/g) | KSOS concentration (mg/g) | [HA]/[SOS] Ratio | % of loss in the viscosity, with respect to the reference composition |
|---|---|---|---|
| 25 | 0 | — | — |
| 25 | 0.01 | 2500 | 0 |
| 25 | 0.05 | 500 | 0 |
| 20 | 0 | — | — |
| 20 | 10 | 2 | 0 |
| 20 | 20 | 1 | 0 |
| 10 | 0 | — | — |
| 10 | 10 | 1 | 0 |
| 10 | 20 | 0.5 | 0 |
| 4 | 0 | — | — |
| 4 | 40 | 0.1 | 0 |

No loss in the viscosity of the compositions is observed after the autoclaving step of whatever the [HA]/[SOS] ratio.

EXAMPLE 16

Example of test on formulation of KSOS with a gel comprising crosslinked hyaluronic acid at the concentration and at the ratio described in Table 8 below.

The gels are prepared according to the procedure described in Example 2 and are then characterized by rheology according to Example 8.

TABLE 8

Percentage of loss in the elastic component G' after the autoclaving step.

| NaHA concentration (mg/g) | KSOS concentration (mg/g) | [HA]/[SOS] Ratio | % of loss in the elastic component G', with respect to the reference composition |
|---|---|---|---|
| 10.3 | 0 | — | — |
| 10.3 | 25 | 0.4 | 0 |

No loss in the elastic component G' of the compositions is observed after the autoclaving step for an [HA]/[SOS] ratio of 0.4.

The invention claimed is:

1. A sterilized composition, in an aqueous medium, comprising at least one hyaluronic acid and at least one water soluble salt of sucrose octasulphate, wherein the composition is a physical mixture, the ratio by weight of the content of hyaluronic acid [HA] to the content of water-soluble salt of sucrose octasulphate [SOS], [HA]/[SOS], ranges from 0.1 to 2500 and the molecular weight of the hyaluronic acid ranges from 0.01 MDa to 5 MDa.

2. The composition according to claim 1, wherein, when it is analyzed by proton $^1$H NMR spectroscopy, the value of the chemical shift of the anomeric proton of the salt of sucrose octasulphate is identical to the value of the chemical shift of the anomeric proton of the salt of sucrose octasulphate alone in solution.

3. The composition according to claim 1, wherein the content of hyaluronic acid ranges from 2 mg/g to 50 mg/g of composition.

4. The composition according to claim 1, wherein the content of hyaluronic acid is ranges from 4 mg/g to 40 mg/g of composition.

5. The composition according to claim 1, wherein it comprises at least one non-crosslinked hyaluronic acid.

6. The composition according to claim 1, wherein it additionally comprises at least one crosslinked hyaluronic acid.

7. The composition according to claim 6, wherein the crosslinked hyaluronic acid exhibits a degree of crosslinking X ranges from 0.001 to 0.5.

8. The composition according to claim 1, wherein it comprises at least one hyaluronic acid substituted by a group contributing lipophilic or hydrophilic properties.

9. The composition according to claim 1, wherein it additionally comprises another polysaccharide.

10. The composition according to claim 1, wherein the water-soluble salt of sucrose octasulphate is selected from the group consisting of alkali metal salts, alkaline earth metal salts, silver salts, the ammonium salts and amino acid salts.

11. The composition according to claim 10, wherein the water-soluble salt of sucrose octasulphate is selected from the group consisting of the alkali metal salts and the alkaline earth metal salts.

12. The composition according to claim 9, wherein the water-soluble salt of sucrose octasulphate is the sodium salt of sucrose octasulphate or the potassium salt of sucrose octasulphate.

13. The composition according to claim 1, wherein the content of water-soluble salt of sucrose octasulphate ranges from 0.01 mg/g to 40 mg/g of composition.

14. The composition according to claim 1, wherein that it additionally comprises at least one active principle.

15. The composition according to claim 14, wherein the active principle is chosen from antioxidants, local anesthetics or vitamins, alone or in combination.

16. The composition according to claim 15, wherein the antioxidants are chosen from polyols.

17. The composition according to claim 15, wherein the local anesthetics are selected from the group consisting of lidocaine, procaine, mepivacaine, ropivacaine, bupivacaine and their pharmaceutically acceptable salts.

18. The composition according to claim 14, wherein the content of active principle(s) is comprised between 0.01 and 10% by weight, with respect to the total weight of the composition.

19. A process for the manufacture of a composition according to claim 1, wherein it comprises at least:
    a hydration step of fibers of at least one hyaluronic acid, in order to obtain a hydrogel,
    a mixing step of a solution of water-soluble salt of sucrose octasulphate with the hydrogel obtained in the preceding step,
    a homogenization step, and
    a steam autoclaving step.

20. A process for the manufacture of a composition according to claim 18, wherein it additionally comprises at least one crosslinking step.

21. A viscosupplementation composition comprising the composition according to claim 1.

22. A dermal filler comprising the composition according to claim 1.

23. A composition for the treatment of ocular dryness comprising the composition according to claim 1.

24. A cosmetic formulation, wherein it comprises the sterilized composition according to claim 1 and at least one cosmetically acceptable excipient.

25. The cosmetic formulation according to claim 24, wherein it comprises, from 0.01 to 10% by weight, with respect to the total weight of the cosmetic formulation, of the sterilized composition.

26. A kit comprising a composition according to claim 1, packaged in sterilized syringes or in sterilized single-dose bottles.

* * * * *